(12) United States Patent
Anderson et al.

(10) Patent No.: US 8,273,066 B2
(45) Date of Patent: Sep. 25, 2012

(54) ABSORBENT ARTICLE WITH HIGH QUALITY INK JET IMAGE PRODUCED AT LINE SPEED

(75) Inventors: Kimberly D. Anderson, Neenah, WI (US); Michael J. Garvey, Appleton, WI (US); Melissa C. Putzer, Oshkosh, WI (US); Timothy J. Probst, Neenah, WI (US); Eric D. Johnson, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1377 days.

(21) Appl. No.: 10/623,030

(22) Filed: Jul. 18, 2003

(65) Prior Publication Data

US 2005/0015066 A1  Jan. 20, 2005

(51) Int. Cl.
*A61F 13/15* (2006.01)
*A61F 13/20* (2006.01)

(52) U.S. Cl. .............. 604/385.01; 604/361; 604/367

(58) Field of Classification Search ............ 604/361, 604/385.01, 358; 428/207; 347/68
See application file for complete search history.

(56) References Cited

U.S. PATENT DOCUMENTS

| | | | |
|---|---|---|---|
| 1,366,789 A | 1/1921 | Graham | |
| 3,019,932 A | 2/1962 | Singiser | |
| 3,338,992 A | 8/1967 | Kinney | |
| 3,341,394 A | 9/1967 | Kinney | |
| 3,467,270 A | 9/1969 | Eady | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| RE28,219 E | 10/1974 | Taylor et al. | |
| 3,849,241 A | 11/1974 | Butin et al. | |
| 3,855,046 A | 12/1974 | Hansen et al. | |
| 4,041,203 A | 8/1977 | Brock et al. | |
| 4,303,924 A | 12/1981 | Young, Jr. | |
| 4,340,563 A | 7/1982 | Appel et al. | |
| 4,374,888 A | 2/1983 | Bornslaeger | |
| 4,382,262 A | 5/1983 | Savit | |
| 4,389,503 A | 6/1983 | Maxwell et al. | |
| 4,478,910 A | 10/1984 | Oshima et al. | |
| 4,503,444 A | 3/1985 | Tacklind | |
| 4,504,357 A | 3/1985 | Holbein et al. | |
| 4,526,825 A | 7/1985 | Whitehead | |
| 4,535,481 A | 8/1985 | Ruth-Larson et al. | |
| 4,680,645 A * | 7/1987 | Dispoto et al. ............ | 358/3.02 |
| 4,689,078 A | 8/1987 | Koike et al. | |

(Continued)

FOREIGN PATENT DOCUMENTS

DE  2313335 B  1/1975

(Continued)

OTHER PUBLICATIONS

RD 173017 A, Head D L, Sep. 10, 1978.

(Continued)

*Primary Examiner* — Michele M Kidwell
(74) *Attorney, Agent, or Firm* — Armstrong Teasdale LLP (57) ABSTRACT

A mass produced absorbent article having an image of a quality that is commercially acceptable. The image is produced by ink jet printheads applying ink to a web moving at high speed under the jets in the course of manufacturing the article. The image is printed at low resolution but is characterized in part by a higher coverage area ratio and brightness.

22 Claims, 8 Drawing Sheets

U.S. PATENT DOCUMENTS

| | | | |
|---|---|---|---|
| 4,786,288 A | | 11/1988 | Handa et al. |
| 4,798,603 A | | 1/1989 | Meyer et al. |
| 4,835,208 A | | 5/1989 | Ball |
| 4,841,310 A | | 6/1989 | Hoffman |
| 4,849,770 A | | 7/1989 | Koike et al. |
| 4,909,879 A | | 3/1990 | Ball |
| 4,969,951 A | | 11/1990 | Koike et al. |
| 5,019,066 A | | 5/1991 | Freeland et al. |
| 5,024,989 A | * | 6/1991 | Chiang et al. ................. 503/227 |
| 5,087,283 A | | 2/1992 | Dixon et al. |
| 5,116,682 A | | 5/1992 | Chakravarti et al. |
| 5,145,727 A | | 9/1992 | Potts et al. |
| 5,151,321 A | | 9/1992 | Reeves et al. |
| 5,169,706 A | | 12/1992 | Collier, IV et al. |
| 5,178,931 A | | 1/1993 | Perkins et al. |
| 5,188,885 A | | 2/1993 | Timmons et al. |
| 5,195,950 A | | 3/1993 | Delannoy |
| 5,198,833 A | | 3/1993 | Kubota |
| 5,214,442 A | * | 5/1993 | Roller ........................... 347/102 |
| 5,271,883 A | | 12/1993 | Timmons et al. |
| 5,280,310 A | | 1/1994 | Otsuka et al. |
| 5,371,520 A | | 12/1994 | Kubota |
| 5,429,629 A | | 7/1995 | Latimer et al. |
| 5,458,590 A | | 10/1995 | Schleinz et al. |
| 5,464,688 A | | 11/1995 | Timmons et al. |
| 5,466,232 A | | 11/1995 | Cadieux et al. |
| 5,487,614 A | | 1/1996 | Hale |
| 5,490,846 A | | 2/1996 | Ellis et al. |
| 5,503,076 A | * | 4/1996 | Yeo ................................ 101/483 |
| 5,522,810 A | | 6/1996 | Allen, Jr. et al. |
| 5,562,037 A | | 10/1996 | Schleinz et al. |
| 5,562,650 A | | 10/1996 | Everett et al. |
| 5,563,642 A | | 10/1996 | Keefe et al. |
| 5,571,586 A | | 11/1996 | Gobran |
| 5,591,153 A | | 1/1997 | Mattingly, III |
| 5,594,955 A | | 1/1997 | Sommers |
| 5,597,642 A | | 1/1997 | Schleinz et al. |
| 5,601,320 A | | 2/1997 | Miller |
| 5,601,325 A | | 2/1997 | Sokaski |
| 5,601,326 A | | 2/1997 | Smetz |
| 5,601,327 A | | 2/1997 | Cho |
| 5,612,118 A | * | 3/1997 | Schleinz et al. ........... 428/195.1 |
| 5,648,805 A | | 7/1997 | Keefe et al. |
| 5,681,645 A | | 10/1997 | Strack et al. |
| 5,695,855 A | | 12/1997 | Yeo et al. |
| 5,695,868 A | | 12/1997 | McCormack |
| 5,705,251 A | | 1/1998 | Morman et al. |
| 5,720,738 A | | 2/1998 | Clark |
| 5,755,906 A | | 5/1998 | Achter et al. |
| 5,757,391 A | | 5/1998 | Hoisington |
| 5,759,673 A | | 6/1998 | Ikezawa et al. |
| 5,762,642 A | | 6/1998 | Coles et al. |
| 5,769,837 A | | 6/1998 | Parr |
| H1746 H | | 8/1998 | Carrier et al. |
| 5,797,894 A | | 8/1998 | Cadieux et al. |
| 5,807,365 A | | 9/1998 | Luceri |
| 5,851,274 A | | 12/1998 | Lin |
| 5,851,595 A | | 12/1998 | Jones, Jr. |
| 5,853,859 A | | 12/1998 | Levy et al. |
| 5,895,505 A | | 4/1999 | Yamamoto et al. |
| 5,931,824 A | | 8/1999 | Stewart et al. |
| 5,959,641 A | | 9/1999 | Yokoi |
| 5,972,082 A | | 10/1999 | Koyano et al. |
| 5,985,396 A | | 11/1999 | Kerins et al. |
| 6,013,347 A | | 1/2000 | Martin et al. |
| 6,020,405 A | | 2/2000 | Matzinger et al. |
| 6,024,220 A | | 2/2000 | Smith et al. |
| 6,037,281 A | | 3/2000 | Mathis et al. |
| 6,050,666 A | | 4/2000 | Yeoh et al. |
| 6,051,036 A | | 4/2000 | Kusaki et al. |
| 6,096,412 A | * | 8/2000 | McFarland et al. ......... 428/211.1 |
| 6,103,364 A | | 8/2000 | Harris et al. |
| 6,106,922 A | | 8/2000 | Cejka et al. |
| 6,120,888 A | | 9/2000 | Dolsey et al. |
| 6,132,858 A | | 10/2000 | Kloos |
| 6,141,799 A | | 11/2000 | Morris |
| 6,142,984 A | | 11/2000 | Brown et al. |
| 6,146,770 A | | 11/2000 | Sargeant et al. |
| 6,149,259 A | | 11/2000 | Otsuka et al. |
| 6,150,005 A | | 11/2000 | Williams et al. |
| 6,159,581 A | | 12/2000 | Yoneda et al. |
| 6,199,968 B1 | | 3/2001 | Katakura et al. |
| 6,235,098 B1 | | 5/2001 | Maekawa et al. |
| 6,235,659 B1 | | 5/2001 | McAmish et al. |
| 6,245,410 B1 | | 6/2001 | Hähnle et al. |
| 6,254,582 B1 | | 7/2001 | O'Donnell et al. |
| 6,258,427 B1 | | 7/2001 | Kerins et al. |
| 6,263,816 B1 | | 7/2001 | Codos et al. |
| 6,264,641 B1 | | 7/2001 | Van Gompel et al. |
| 6,265,053 B1 | | 7/2001 | Kronzer et al. |
| 6,266,436 B1 | | 7/2001 | Bett et al. |
| H1978 H | | 8/2001 | Freiburger et al. |
| 6,297,424 B1 | * | 10/2001 | Olson et al. ................... 604/361 |
| 6,316,688 B1 | | 11/2001 | Hammons et al. |
| 6,383,960 B1 | | 5/2002 | Everett et al. |
| 6,395,957 B1 | | 5/2002 | Chen et al. |
| 6,450,627 B1 | | 9/2002 | Moyniham et al. |
| 6,477,948 B1 | * | 11/2002 | Nissing et al. ................ 101/211 |
| 6,680,784 B1 | * | 1/2004 | Nomura et al. .............. 358/1.15 |
| 2003/0044578 A1 | * | 3/2003 | Nissing ......................... 428/141 |

FOREIGN PATENT DOCUMENTS

| | | |
|---|---|---|
| DE | 2340855 B | 6/1975 |
| DE | 2654823 A | 6/1978 |
| DE | 2412852 B | 5/1979 |
| DE | 19803827 A1 | 8/1999 |
| DE | 19810847 A1 | 9/1999 |
| DE | 19810849 C2 | 5/2000 |
| EP | 0 023 433 A2 | 2/1981 |
| EP | 0 304 957 B2 | 3/1989 |
| EP | 0344070 A1 | 11/1989 |
| EP | 0355795 A1 | 2/1990 |
| EP | 0 639 459 A2 | 2/1995 |
| EP | 0711538 A1 | 5/1996 |
| EP | 0 471 384 B1 | 10/1996 |
| EP | 0 747 029 A1 | 12/1996 |
| EP | 0 713 744 B1 | 3/1998 |
| EP | 0930056 A2 | 7/1999 |
| EP | 1 059 340 A1 | 12/2000 |
| EP | 1 070 596 A2 | 1/2001 |
| EP | 1 164 007 A1 | 12/2001 |
| EP | 0 861 154 B1 | 4/2002 |
| EP | 1 062 095 B1 | 6/2002 |
| EP | 0 764 550 B1 | 11/2002 |
| EP | 1295711 A1 | 3/2003 |
| EP | 0 809 680 B2 | 5/2003 |
| EP | 0 805 027 B1 | 9/2003 |
| EP | 1646347 A1 | 4/2006 |
| FR | 2741296 A1 | 5/1997 |
| GB | 2 128 439 A | 4/1984 |
| GB | 2 334 684 A | 9/1999 |
| JP | 55051583 A | 4/1980 |
| JP | 57115352 A | 7/1982 |
| JP | 60104076 A | 6/1985 |
| JP | 85027588 B | 6/1985 |
| JP | 60169489 A | 9/1985 |
| JP | 60245557 A | 12/1985 |
| JP | 61118473 A | 6/1986 |
| JP | 61179269 A | 8/1986 |
| JP | 61179271 A | 8/1986 |
| JP | 61179272 A | 8/1986 |
| JP | 61179273 A | 8/1986 |
| JP | 63265680 A | 11/1988 |
| JP | 01013518 A | 1/1989 |
| JP | 03104646 A | 5/1991 |
| JP | 03049311 B4 | 7/1991 |
| JP | 92015746 B | 3/1992 |
| JP | 04251747 A | 9/1992 |
| JP | 04292947 A | 10/1992 |
| JP | 05035191 B4 | 5/1993 |
| JP | 05230409 A | 9/1993 |
| JP | 05247390 A | 9/1993 |
| JP | 05331396 A | 12/1993 |
| JP | 06127032 A | 5/1994 |
| JP | 06246934 A | 9/1994 |
| JP | 06286134 A | 10/1994 |
| JP | 06312509 A | 11/1994 |

| | | | |
|---|---|---|---|
| JP | 07034019 A | 2/1995 |
| JP | 07068922 A | 3/1995 |
| JP | 07089077 A | 4/1995 |
| JP | 07125197 A | 5/1995 |
| JP | 07156407 A | 6/1995 |
| JP | 07213310 A | 8/1995 |
| JP | 07241983 A | 9/1995 |
| JP | 07304167 A | 11/1995 |
| JP | 07314694 A | 12/1995 |
| JP | 07314728 A | 12/1995 |
| JP | 07323657 A | 12/1995 |
| JP | 08052903 A2 | 2/1996 |
| JP | 08118617 A | 5/1996 |
| JP | 08164602 A | 6/1996 |
| JP | 08174995 A | 7/1996 |
| JP | 08187933 A | 7/1996 |
| JP | 08216395 A | 8/1996 |
| JP | 08259868 A | 10/1996 |
| JP | 08267733 A | 10/1996 |
| JP | 08309987 A | 11/1996 |
| JP | 09031866 A | 2/1997 |
| JP | 09039233 A | 2/1997 |
| JP | 02593830 B2 | 3/1997 |
| JP | 09057966 A | 3/1997 |
| JP | 09066661 A | 3/1997 |
| JP | 09175004 A | 7/1997 |
| JP | 09175005 A | 7/1997 |
| JP | 09175006 A | 7/1997 |
| JP | 09175007 A | 7/1997 |
| JP | 09194781 A | 7/1997 |
| JP | 09226229 A | 9/1997 |
| JP | 09240138 A | 9/1997 |
| JP | 09268482 A | 10/1997 |
| JP | 09268484 A | 10/1997 |
| JP | 02618359 B2 | 11/1997 |
| JP | 09286102 A | 11/1997 |
| JP | 09314984 A | 12/1997 |
| JP | 10034967 A | 2/1998 |
| JP | 10044408 A | 2/1998 |
| JP | 02732999 B2 | 3/1998 |
| JP | 02758788 B2 | 5/1998 |
| JP | 10138504 A | 5/1998 |
| JP | 10138510 A | 5/1998 |
| JP | 10138516 A | 5/1998 |
| JP | 10138520 A | 5/1998 |
| JP | 10138521 A | 5/1998 |
| JP | 10193610 A | 7/1998 |
| JP | 10264498 A | 10/1998 |
| JP | 10278312 A | 10/1998 |
| JP | 11010852 A | 1/1999 |
| JP | 11010853 A | 1/1999 |
| JP | 11061021 A | 3/1999 |
| JP | 11099646 A | 4/1999 |
| JP | 11188968 A | 7/1999 |
| JP | 11207951 A | 8/1999 |
| JP | 11268284 A | 10/1999 |
| JP | 11268405 A | 10/1999 |
| JP | 11277772 A | 10/1999 |
| JP | 2000000266 A | 1/2000 |
| JP | 2000043401 A | 2/2000 |
| JP | 2000052640 A | 2/2000 |
| JP | 2000127611 A | 5/2000 |
| JP | 2000190628 A | 7/2000 |
| JP | 2000203150 A | 7/2000 |
| JP | 2000233571 A | 8/2000 |
| JP | 03089308 B2 | 9/2000 |
| JP | 03089583 B2 | 9/2000 |
| JP | 2000238410 A | 9/2000 |
| JP | 2000256974 A | 9/2000 |
| JP | 2000296670 A | 10/2000 |
| JP | 2001010031 A2 | 1/2001 |
| JP | 2001018518 A2 | 1/2001 |
| JP | 2001020185 A2 | 1/2001 |
| JP | 2001039017 A2 | 2/2001 |
| NL | 9400024 A | 8/1995 |
| WO | WO 99/33669 | 7/1999 |
| WO | WO 99/43760 | 9/1999 |
| WO | WO 99/60973 | 12/1999 |
| WO | WO 99/65700 | 12/1999 |
| WO | WO 00/35401 | 6/2000 |
| WO | WO 00/40195 | 7/2000 |
| WO | WO 00/42960 | 7/2000 |
| WO | WO 00/56972 | 9/2000 |
| WO | WO 00/69950 | 11/2000 |
| WO | WO 00/72984 A1 | 12/2000 |
| WO | WO 00/73063 A1 | 12/2000 |
| WO | WO 00/76441 A1 | 12/2000 |
| WO | WO 01/02254 A2 | 1/2001 |
| WO | WO 01/27382 A1 | 4/2001 |
| WO | WO 01/31122 A1 | 5/2001 |
| WO | WO 01/31124 A1 | 5/2001 |
| WO | WO 01/32318 A3 | 5/2001 |
| WO | WO 01/36171 A2 | 5/2001 |
| WO | WO 01/36209 A1 | 5/2001 |
| WO | WO 01/49230 A1 | 7/2001 |
| WO | WO 01/50412 A1 | 7/2001 |
| WO | WO 02/14080 A2 | 2/2002 |
| WO | WO 02/22364 A1 | 3/2002 |
| WO | 2004060683 A1 | 7/2004 |
| WO | 2004064872 A3 | 8/2004 |

OTHER PUBLICATIONS

AATCC Committee RA36/RA38, AATCC 9-Step Chromatic Transference Scale, AATCC Technical Manual, 1999, pp. 378-379.
AATCC Committee RA36, AATCC Test Method 173-1998, CMC: Calculation of Small Color Differences for Acceptability, AATCC Technical Manual, 2001, pp. 309-313.
A.C. Zettlemoryer, Hydrophobic Surfaces, pp. 1-27, F. M. Fowkes, 1969, Academic Press, New York.
A Guide to Understanding Color Communication, X Rite, 2002, 26 pages, United States.
A Guide to Understanding Graphic Arts Densitometry, X Rite, Nov. 2000, 10 pages, United States.
American Society for Testing and Materials (ASTM) Designation: F1571-95, Standard Test Method for Determination of Abrasion and Smudge Resistance of Images Produced from Business Copy Products, Nov. 1995, pp. 1409-1412.
Galaxy PH 256/80 HM, Spectra, Oct. 1, 2002, 2 pages, United States.
Hot Melt Adhesive, Dynamelt® S. Series, The Dynatec Advantage, ITW Dynatec, 1987, 4 pages, United States.
Japanese Unexamined Patent Application No. 2000-266, Official Gazette for Unexamined Patent Applications, Filed Jun. 16, 1998, 21 pages, Japan.
Material Safety Data Sheet, Hot Melt Ink, Black, High; JET 7520/JET7533; pp. 1-4.
Material Safety Data Sheet, Hot Melt Ink, Cyan, Magenta, Yellow, etc.; pp. 1-3.
Pond, Stephen F., Ink Jet Technology and Product Development Strategies, 2000, pp. 198-201, 377-385, Torrey Pines Research.
Shaw, Duncan J., Introduction to Colloid and Surface Chemistry, Third Edition, 1980, pp. 131-135, Butterworths.
Southworth, Miles, Pocket Guide to Color Reproduction, Communication and Control, 1972, pp. 1-7, Graphic Arts.
938 Graphic Arts Spectrodensitometer, X Rite, 2 pages, United States.
948/968 Color Measurement Instruments, Operation Manual, X Rite, 1999, 73 pages, United States.
International Search Report re PCT/US2004/010201, 4 pages.

* cited by examiner

ABSORBENT ARTICLE WITH HIGH QUALITY INK JET IMAGE PRODUCED AT LINE SPEED

BACKGROUND OF THE INVENTION

This invention relates generally to printed images for mass produced articles, and more particularly to an absorbent article with a high quality ink jet image made on a fast moving substrate during assembly of the article.

Graphics are commonly printed on articles of manufacture to increase their aesthetic appeal. One example of this is graphics or images printed on absorbent garments, such as infant and children's diapers and training pants. The outer covers of these articles are nearly always imprinted with brightly colored images in the form of designs and characters that are pleasing to the child and caregiver. However, images may also be printed on other absorbent articles such as feminine healthcare products, adult incontinence garments and bandages. The article need not relate to personal care, and could be for example, a cleaning wipe.

Traditionally, imprinting the outer cover material, or a portion of the article with an image has been carried out by flexographic and rotogravure printing techniques prior to assembly of the absorbent garment. For example, outer cover material pre-printed with the image may be moved or shipped to the location where the absorbent garment is assembled and fed into the assembly apparatus. Certain inefficiencies arise from printing the images off line from the general assembly process through the shipping and handling of the outer cover material. However, printing the image in the manufacturing line has not been practical because it is difficult, time-consuming, and costly to change the printed image with traditional flexographic and rotogravure or other contact printing processes. The ability to change the image being printed is very limited and if a change is made, the entire assembly process must be shut down. Additionally, these types of printing processes create a significant amount of waste and delay during starting and stopping and other transitory process changes, and therefore do not lend themselves to the manufacture of mass produced articles.

Further, the types of materials that have utility in mass produced articles such as diapers, often have properties that can complicate flexographic or rotogravure printing. For example, the materials may be porous, thermally sensitive, stretchable/elastic, or unstable in the machine direction. Moreover, the materials may have low tensile properties, embossing or three dimensional topography, or surface tensions that are not compatible with inks (e.g., being hydrophobic or hydrophilic). Also these processes require contact to transfer the ink to the web, which often causes distorted, smeared, or unclear images.

Ink jet non-contact printing systems are known to provide flexibility in image printing. Change from one image to the next can be done rapidly, and even on the fly. Drop on demand piezoelectric ink jet printing apparatus have been used to apply inks to a variety of substrates. Generally, a drop on demand piezoelectric ink jet printing apparatus discharges small individual droplets of ink onto a substrate in a predetermined pattern. In this type of apparatus the printhead does not contact the web on which it prints. Such an apparatus typically incorporates a printhead having an array of orifices in a block, and a controller. The orifices are customarily arranged in a row in closely spaced relation. The printheads are controlled by the controller, which can be keyed by an operator to operate the printhead according to a programmed schedule to print one or a series of images.

Each orifice is designed to emit a single droplet of ink each time its associated printhead fires. The droplets, emitted according to the programmed sequence, are directed toward a substrate and form a dot. The image is built up from these dots. The quality of print produced by a drop on demand ink jet printer requires among other things, a certain area of coverage of the substrate by the ink. Thus, it is desirable for a greater surface area of the web to be covered by a given amount of applied ink, and for there to be a higher number of dots per unit area (i.e., dots per inch or "dpi"). However when the substrate is running under the orifices at high speed (e.g., 366 meters per minute (1,200 feet per minute) or greater), it is very difficult for the printhead to fire rapidly enough to put down a large number of dots per inch. This is particularly true where, as a result of the operation of the absorbent garment assembly apparatus, the image must be formed in a single pass of the material on which the images are formed under the ink jet printheads.

Heretofore, images formed at production line speeds by piezoelectric jet printers of the type described have been unsatisfactory. To achieve images of the necessary quality with ink jet printers, it has conventionally been necessary to use multiple passes of the printhead over the substrate and resolutions greater than 300 dpi. Among other problems, a substantial quantity of ink is used which drives up cost. Moreover as mentioned above, conventional ink jet printing processes have not been successful in producing commercially acceptable images where the substrate moves rapidly (e.g., 100 fpm and more) beneath the printheads. While there has been progress in the area of ink jet printing, the ink jet printers have been limited in that they were not able to produce an image of a commercially acceptable quality at the line speeds encountered in the assembly of an absorbent garment such as a diaper or training pant.

SUMMARY OF THE INVENTION

The present invention provides a compliant laminate, or more particularly, an absorbent article with an image of high quality. This image may be formed during the assembly of the laminate or article at high line speeds.

In one aspect of the invention, a mass produced absorbent article comprises an absorbent member adapted to retain liquid therein, at least one other component operatively connected to the absorbent member in a unit, and an image. The image includes at least one ink having the color of one of cyan, magenta, yellow and black. The image is printed in a non-contact manner on at least a portion of said one component by ink jets at a resolution of about 100 dpi with said component moving under the ink jets at a speed of at least about 30.5 mpm (100 fpm). Any area in the image having a cyan colored ink applied at maximum threshold thereto has a coverage area ratio of cyan colored ink of at least about 3%, any area in the image having a magenta colored ink applied at maximum threshold thereto has a coverage area ratio of magenta colored ink of at least about 5%, any area in the image having a yellow colored ink applied at maximum threshold thereto has a coverage area ratio of yellowed colored ink of at least about 6%, and any area in the image having a black colored ink applied at maximum threshold thereto has a coverage area ratio of black colored ink of at least about 6%.

In another aspect of the invention, a mass produced compliant laminate comprises multiple layers operatively connected together in a laminate unit, and an image including at least one ink having the color of one of cyan, magenta, yellow and black. The image is printed in a non-contact manner on at least a portion of one of the layers by ink jets at a resolution of about 100 dpi with said one layer moving under the ink jets at a speed of at least about 30.5 mpm (100 fpm). Any cyan, magenta, yellow or black colors in the image applied at maximum threshold having the coverage area ratios as set forth above.

In a still further aspect of the present invention, a mass produced absorbent article comprises an absorbent member adapted to retain liquid therein, at least one other component operatively connected to the absorbent member in a unit, and an image including at least one process color ink. The image is printed in a non-contact manner on at least a portion of said one component by ink jets. The image includes at least one separable design element outlined in one selected color and being free of said selected color as shading in an interior of the design element. The design element has a height of no less than about 0.64 centimeters (0.25 inch).

In another aspect of the present invention, a mass produced absorbent article comprises an absorbent member adapted to retain liquid therein, at least one other component operatively connected to the absorbent member in a unit, and an image including at least one ink having the color of one of cyan, magenta, yellow and black. The image is printed in a non-contact manner on at least a portion of said component by ink jets at a resolution of about 100 dpi with the outer cover moving under the ink jets at a speed of at least about 30.5 mpm (100 fpm). A color difference (DE*) value for any cyan colored ink in the image as compared to a background color of said component on which the image is printed is at least about 6, the DE* value for any magenta colored ink in the image has a color difference (DE*) of at least about 9, the DE* value for any yellow colored ink in the image has a color difference (DE*) of at least about 8, and the DE* value for any black colored ink in the image has a color difference (DE*) of at least about 6.

Other features of the invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE DRAWINGS

Figure 1:
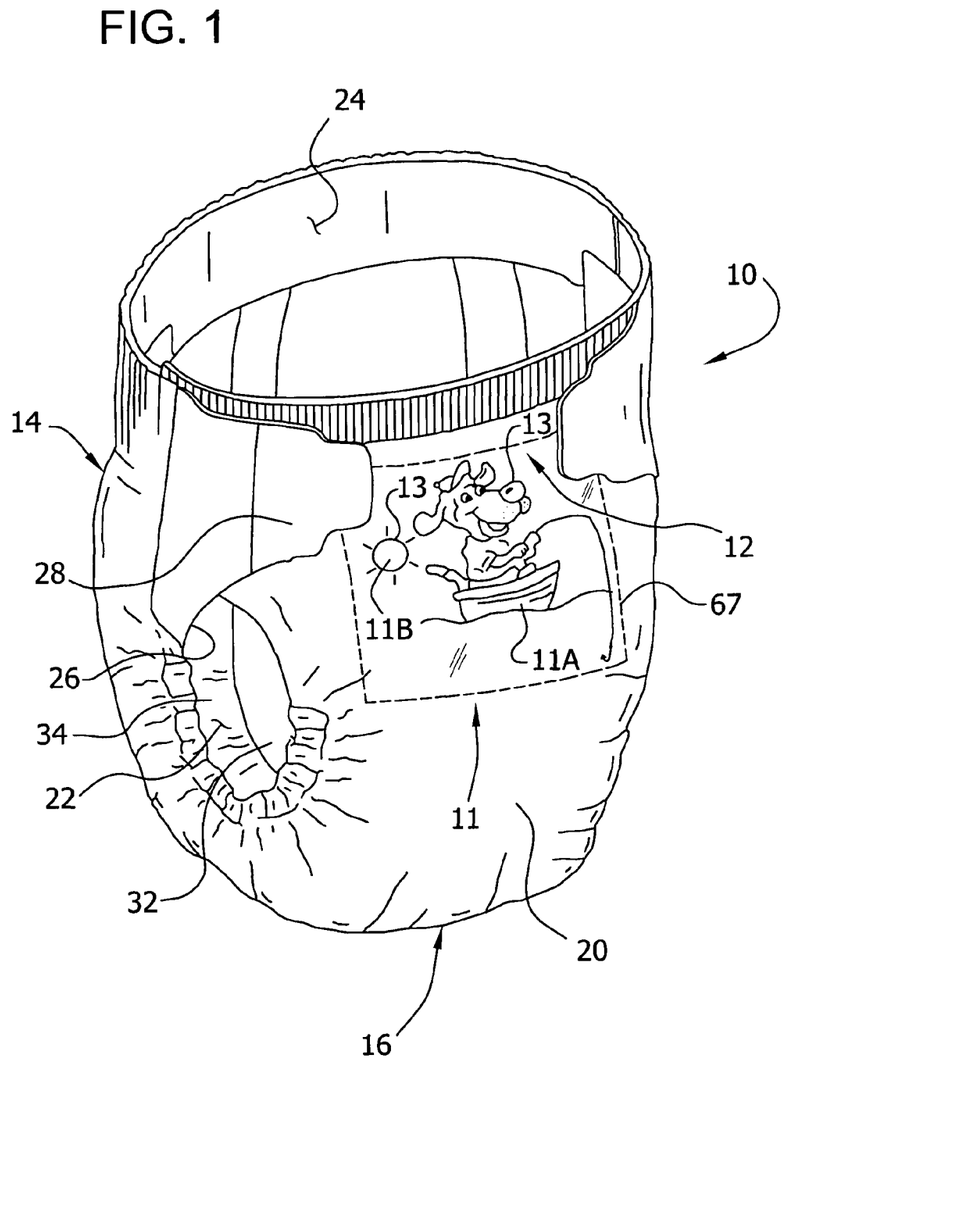
FIG. 1 is a perspective of a diaper having an image on an outer cover thereof.

Referring now to the drawings and in particular to FIG. 1, an absorbent garment in the form of a diaper (indicated generally at 10) having an image 11 of the present invention is shown. It will be readily appreciated that the image 11 of the present invention is not limited to diapers, absorbent garments or personal care products. The diaper 10 comprises a front waist region 12, a back waist region 14, and an intermediate crotch region 16 interconnecting the front and back waist regions (the numbers designating their subject generally). The waist regions 12 and 14 comprise those portions of the diaper 10 which when worn, wholly or partially cover or encircle the waist or mid-lower torso of the wearer. The intermediate crotch region 16 lies between and interconnects the waist regions 12 and 14, and comprises that portion of the article 10 which, when worn, is positioned between the legs of the wearer (not shown) and covers the lower torso of the wearer. The exterior of the diaper 10 is formed substantially by an outer cover 20 constructed to form a liquid barrier.

The diaper 10 has a three-dimensional configuration, as fastened on a wearer (FIG. 1). In this configuration the diaper has an interior space 22 for receiving the lower torso of a person wearing the diaper, a waist opening 24 for receiving the wearer into the interior space of the diaper, and a pair of leg openings 26 (only one is shown). Fastener tabs 28 are attached to a back waist region 14 of the diaper. These tabs 28 may be releasably attached to the front waist region 12 of the diaper 10 for securing the diaper around the lower torso of the wearer. Other fastening systems (not shown) may be employed without departing from the scope of the present invention.

The diaper 10 generally includes a bodyside liner 32 on its innermost surface that contacts the skin of the person wearing the diaper 10. The liner 32 is desirably a soft, compliant material which is highly liquid permeable and hydrophobic to permit passage of liquid through the liner and to maintain a relatively dry surface contacting the skin. These types of materials are well known to those or ordinary skill in the art and will not be more fully described herein. Between the bodyside liner 32 and the outer cover 20, there is some form of liquid retention structure (not shown), such as an absorbent pad made of fibrous absorbent material and superabsorbent material (SAM). An example of such an absorbent pad is shown in co-assigned U.S. Pat. No. 6,383,960, entitled LAYERED ABSORBENT STRUCTURE, which issued on May 7, 2002. There is also typically a surge layer (not shown) of material that rapidly absorbs liquid passing through the bodyside liner. The surge layer can distribute the liquid over a larger surface area before releasing it to the absorbent pad. Suitable surge layers are described in co-assigned U.S. Pat. Nos. 4,798,603, 5,364,382, 5,429,629, 5,490,846, 5,522,810 and 5,562,650.

To further enhance containment and/or absorption of body exudates, the article 10 may include a front waist elastic member, a rear waist elastic member, and leg elastic members, as are known to those skilled in the art. The waist elastic members can be operatively joined to the outer cover 20 and/or body side liner 32 along opposite waist edges, and can extend over part or all of the waist edges. The leg elastic members are desirably operatively joined to the outer cover 20 and/or body side liner 32 along opposite side edges of the diaper 10 and positioned in the crotch region 16 of the diaper.

The waist elastic members and the leg elastic members can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and attached to a substrate, attached to a gathered substrate, or attached to a substrate and then elasticized or shrunk, for example with the application of heat; such that elastic constrictive forces are imparted to the substrate. In one particular embodiment, for example, the leg elastic members include a plurality of dry-spun coalesced multifilament spandex elastomeric threads sold under the trade name LYCRA® and available from E.I. DuPont de Nemours and Company, Wilmington, Del., U.S.A.

To still further enhance containment and/or absorption of any body exudates discharged from the wearer, the diaper 10 may include a pair of containment flaps 34 (only one is shown) which are configured to provide a barrier to the transverse flow of body exudates. A flap elastic member (not shown) may be operatively joined with each containment flap 34 in any suitable manner as is well known in the art. The elasticized containment flaps 34 define an unattached edge that assumes an upright, generally perpendicular configuration in at least the crotch region 16 of the diaper 10 to form a seal against the wearer's body. The containment flaps 34 can be located along the transversely opposed side edges of the diaper 10, and can extend longitudinally along substantially the entire length of the diaper or may only extend partially along the length of the diaper. Suitable constructions and arrangements for the containment flaps 34 are generally well known to those skilled in the art.

The outer cover 20 desirably comprises a material which is substantially liquid impermeable, and can be elastic, extensible or nonstretchable. The outer cover 20 can be a single layer of liquid impermeable material, but desirably comprises a multi-layered laminate structure in which at least one of the layers is liquid impermeable. For instance, the outer cover 20 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of the same materials as the liquid permeable bodyside liner 32. While it is not a necessity for the outer layer of the outer cover 20 to be liquid permeable, it is desired that it provides a relatively cloth-like texture to the wearer.

The inner layer (not shown) of the outer cover 20 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover when a single layer, prevents waste material from wetting articles, such as bed sheets and clothing, as well as the wearer and caregiver. A suitable liquid impermeable film for use as a liquid impermeable inner layer, or a single layer liquid impermeable outer cover 20, is a 0.02 millimeter (0.001 inches) polyethylene film commercially available from Pliant Corporation of Schaumburg, Ill., U.S.A.

If the outer cover is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A. A description of alternative outer cover materials made of extensible materials (so that the outer covers are expandable) can be found in co-assigned U.S. Pat. No. 6,264,641, entitled EXPANDABLE COVER GARMENT, issued Jul. 24, 2001.

Figure 6A:
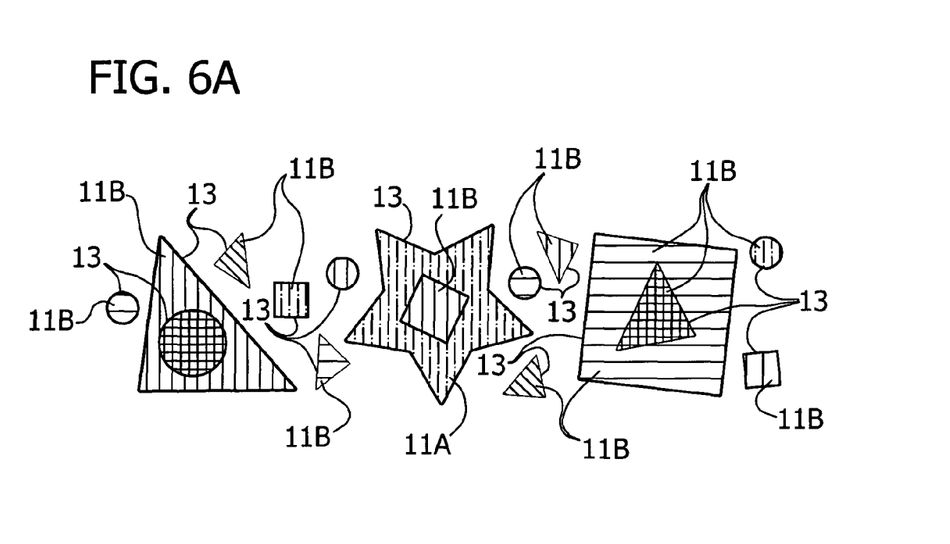
FIGS. 6A and 6B are images including geometric shapes.
Figure 6B:
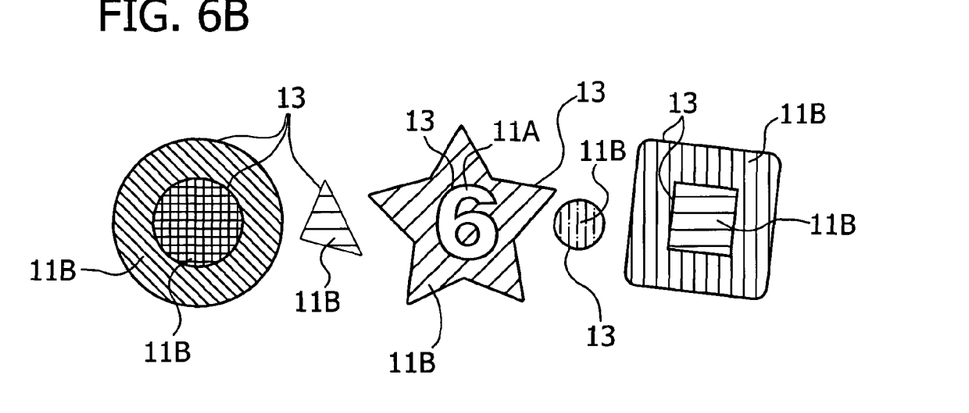
Figure 6C:
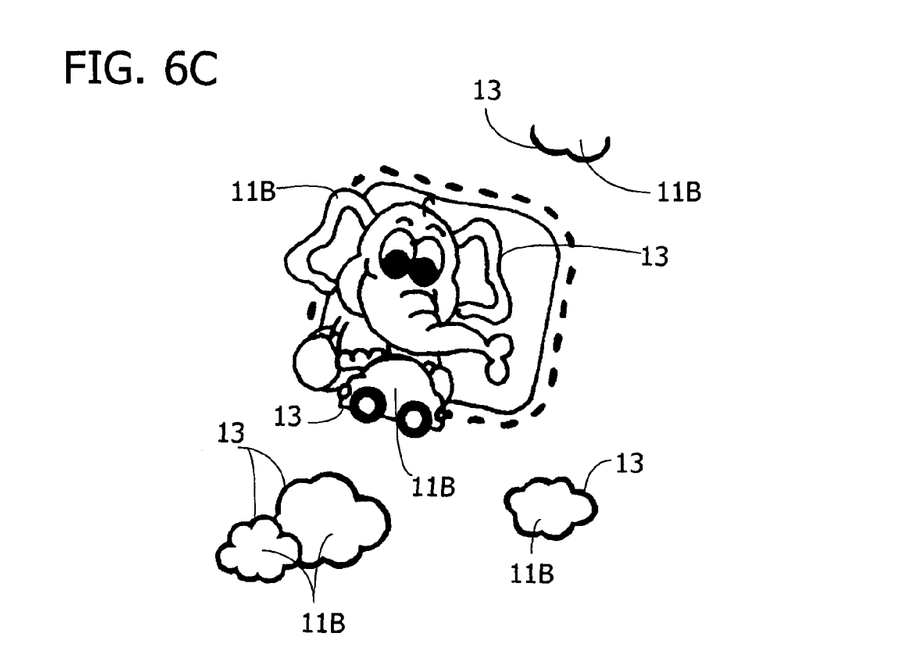
FIGS. 6C and 6D are images including elephant characters.
Figure 6D:
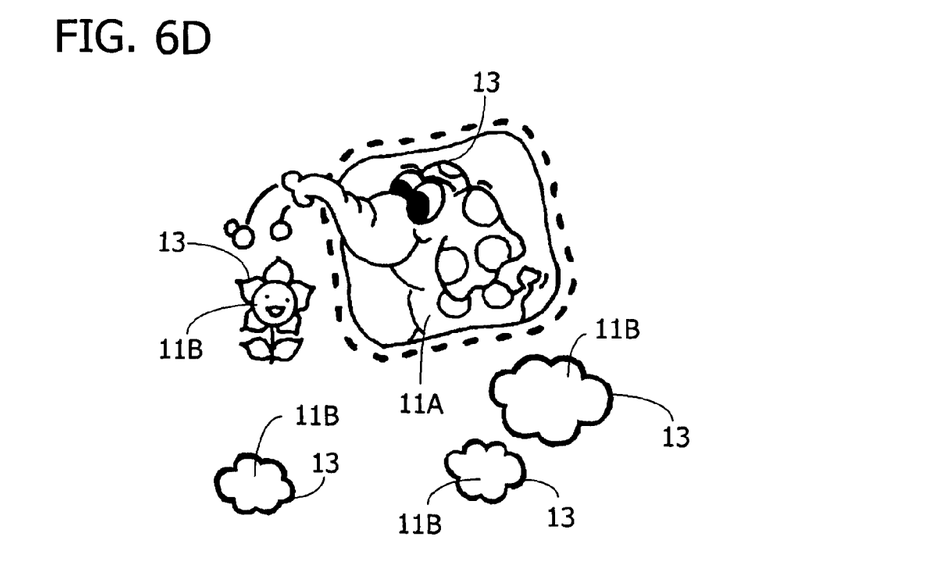

The diaper 10 has the graphic or image (generally indicated at 11) printed on a front portion of the outer layer of the outer cover 20 of the diaper. In the illustrated embodiment, the outer cover 20 provides a white background on which the image 11 is printed. However, it is to be understood that the background could be other, non-white colors, such as a color selected for making colors in the image stand out. The image 11 includes two separable design elements, namely a fishing dog and boat (11A) and the sun (11B). Generally speaking, a design element is a representation in the image of a living thing, manmade thing, or naturally occurring visually perceptible thing that is perceived by the ordinary observer as being separate and distinct from its surroundings. It will be understood that the precise location of the image may be other than described for the illustrated embodiment without departing from the scope of the present invention. This includes printing on any other components of the article. Examples of other images are shown in FIGS. 6A-6D. FIGS. 6A and 6B show an image made up of basic geometrical shapes. FIGS. 6C and 6D show an elephant character with clouds and either a car (FIG. 6C) or a flower (FIG. 6D). In each figure, the design elements other than the focal design element are labeled 11B and the focal design element is labeled 11A.

Figure 2:
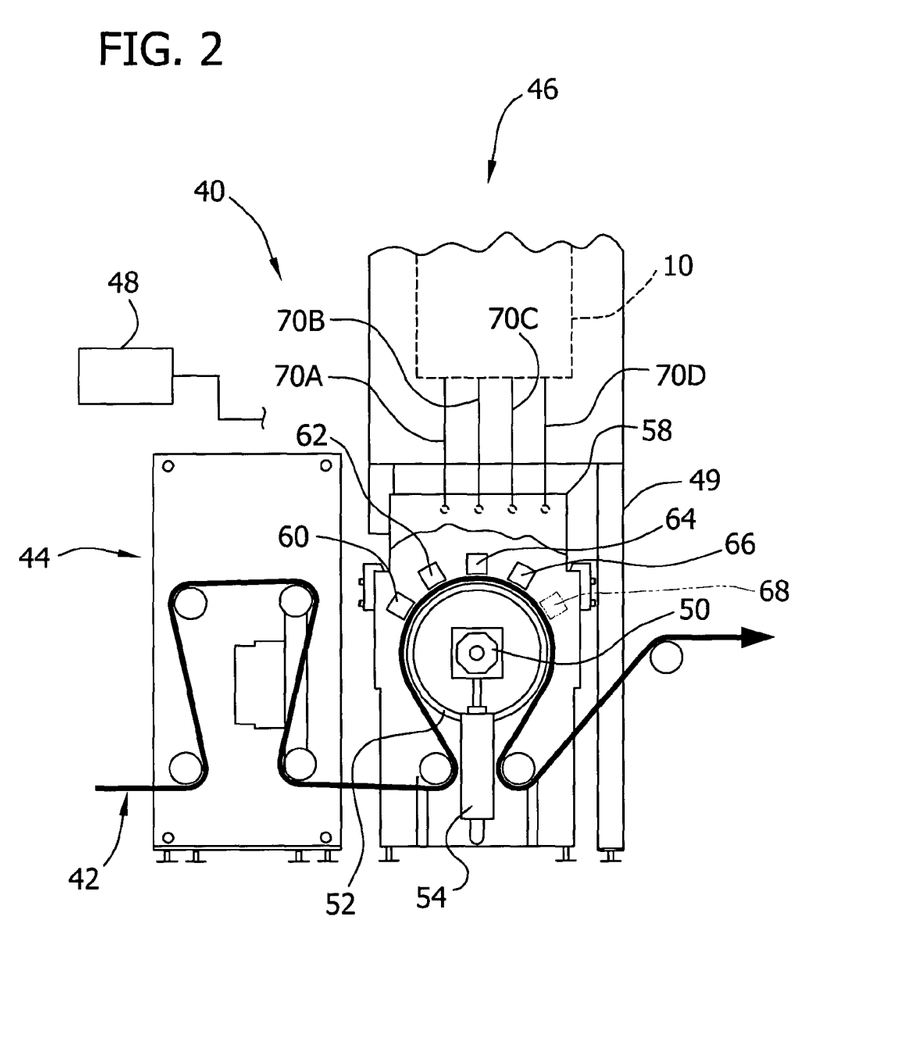
FIG. 2 is a schematic elevation of the printing apparatus used in a diaper assembly line to form the image.

Apparatus (generally indicated at 40) for printing the image shown in FIG. 2 is of a type which prints the outer cover material as it is being fed in web 42 into a diaper assembly line (not shown). Thus, the image is formed in the same process as the assembly of the various components of the diaper 10. However, the image of the present invention may be formed separately from the diaper assembly line without departing from the scope of the present invention. The composition and configuration of diaper assembly lines is well understood by those of ordinary skill in the art. The outer cover material may be fed from a roll (not shown) in the web 42 to a guide 44, then to an ink jet printing station 46 and thereafter to the assembly line. A controller 48 can be used to control the operation of the apparatus 40, and in particular the operation of the ink jet printing station 46. In a particular aspect a web guide 44 can be used to constantly monitor the cross machine direction position of the web 42 to maintain it in a precisely controlled position just prior to entering the printing station 46. An example of a suitable web guide is the Symat 50 Offset Pivot Guide available from Fife Corporation of Oklahoma City, Okla.

The ink jet printing station 46 includes a frame 49 which supports bearings 50 (only one is shown) holding a print drum 52 for rotation about a generally horizontal axis. A suitable bearing would be a model number F4BDL200 manufactured by Dodge Bearings Incorporated of Greenville, S.C. These bearings 50 provide superior resistance to vibration of the drum 52, which is particularly likely to occur during start up and shut down of the diaper assembly apparatus. Vibrations can cause the image to appear fuzzy to the point that diapers would have to be discarded as commercially unacceptable in the absence of vibration control. The bearings 50 supporting the print drum 52 for rotation are mounted for slidingly adjustable vertical movement in the frame 49. Two electrically driven linear motion actuators 54 (only one is shown), on opposite sides of the frame 49, are connected to the print drum bearings 50 for moving the bearings and the print drum 52 relative to the frame. A suitable linear actuator is a Model GSX30 manufactured by Exlar Corporation of Chanhassen, Minn.

An on demand piezoelectric ink jet printing unit includes a housing 58 mounted on the frame 49. The housing 58 supports first through fourth printheads (designated 60, 62, 64, 66, respectively), arranged along an upper portion of the circumference of the print drum 52. The printheads 60-66 are located in a series, one after the other along the circumference portion. The lower ends of the printheads 60-66 (from which the ink droplets are discharged) are all spaced closely with the drum 52. As an example, the printheads 60-66 are spaced from the drum 52 so that the spacing between the upper surface of the outer cover material web 42 and the printheads is between about 1 mm (0.04 in) and about 3mm (0.12 in). In one embodiment, the cylinders 54 move the print drum 52 so that in operation, the spacing of each printhead 60-66 from the web is about 1 mm (0.04 in) to 3mm (0.12 in) in operation, and is larger when not in use for facilitating threading the web 42 of outer cover material through the ink jet printing apparatus 46. Movement is accomplished by the linear actuators 54.

Each printhead 60, 62, 64, 66 applies a respective single color to the web 42. In one embodiment, the printheads are arranged so that the first (most upstream) printhead 60 applies cyan, the second printhead 62 applies magenta, the third printhead 64 applies yellow and the fourth printhead 66 applies black. Cyan, magenta, yellow and black are process inks commonly used for four color ink jet printing. However, it is to be that as used herein "cyan" means true cyan and equivalents thereof, magenta means true magenta and equivalents thereof, yellow, means true yellow and equivalents thereof, and black means true black and equivalents thereof. The arrangement has been found to produce a particularly good image, but the image may be formed by printheads arranged differently and/or applying fewer, more and/or different colors without departing from the scope of the present invention. For example, process colors red, green, blue and white could be used to form images having the same colors.

An overlay 67 may be applied to the outer cover material over the image 11. The overlay 67 is schematically illustrated in FIG. 1. The overlay can be selected to enhance the vibrancy and brightness of the printed image. One way to apply the overlay 67 is by applying clear, non-pigmented ink to the outer cover after the image has been put down by the printhead 60-66. An overlay printhead 68 shown in phantom in FIG. 2 may apply the clear ink to the outer cover material. As illustrated, the overlay printhead 68 is arranged in opposed relationship to the print drum 52.

Although other inks could be used to print the image 11, it has been found that thermochromic or phase change inks, such as wax-based inks have certain advantages in that these inks have reduced tendencies to spread and smear and do not require time or equipment for drying, which are highly desirable in a manufacturing context. These types of inks also do not require the use of solvents that require special environmental controls.

Wax-based inks are received in solid blocks that are melted in an ink supply system 70, schematically illustrated as being mounted on the frame 49. The melted ink of a particular color is fed through a respective one of four lines (designated 70A, 70B, 70C, 70D, respectively) to one of the printheads 60, 62, 64, 66, as demanded by the printhead. One suitable system for melting and supplying the ink is the DYNAMELT® S Series hot melt supply system available from ITW Dynatec of Hendersonville, Tenn. This system is marketed for supplying adhesives and has been modified for supplying melted ink. In one embodiment, the system includes a metered gear pump (not shown) for precise delivery of ink, which gear pump includes stainless steel components in contact with the ink. Moreover, the commercially available system has been further modified by adding a 10 micron filter. Other filter sizes may be used as specified by the printhead vendor or ink vendor. The ink supply system controls the temperature of the ink. In one embodiment, the melted ink is maintained at about 125°. The temperature may be controlled to any level specified by the ink vendors or the printhead vendors.

Suitable printheads 60, 62, 64, 66 that may be used in one embodiment to produce an image according to the present invention are Galaxy PH 256/80 HM 256 channel ink jet printheads (Ser. Nos. 5601320, 5601325, 5601326, 5601327) available from Spectra, Inc. of Lebanon, N.H. These printheads 60-66 each have two piezoelectric crystals with each crystal having two independent electrical circuits. Each circuit is associated with 64 orifices for a total of 256 orifices per printhead. Each of the orifices can be individually addressed so that the controller 48 can select which of the 256 orifices are to be fired in each cycle. The orifices are spaced apart about 0.0254 centimeter (0.01 inch)±0.00245 centimeter (0.001 inch). It will be understood that other printheads having a different number of orifices and/or orifices with different spacings could be used without departing from the scope of the present invention. A longer printhead would allow a wider (in the cross direction of the outer cover material) image to be printed. Moreover, printheads may be banked (placed side-by-side in the cross direction) to print a wider image. The printhead 60-66 each have an ink reservoir on the printhead that has an ink level sensor that can be used to signal the ink supply system 70 to deliver additional ink to the printhead.

The printheads 60, 62, 64, 66 of the ink jet printing unit may desirably be rigidly mounted at precise locations on a bar (not shown) attached to the frame 49. The bar allows all of the printheads 60-66 to be precisely located by locating any one of them. In the illustrated embodiment, the first printhead 60 (i.e., the printhead most upstream relative to the machine direction which is the direction of movement of the cover material web) is the one that is located. This bar (or another suitable fixture precisely locates the printheads 60-66 relative to each other in the machine and cross machine directions, and maintains a precise gap between each printhead orifice and the top surface of the outer cover material web 42. The alignment of the printheads with each other on a centerline is in one instance within from about 0.002 centimeter (0.001 inches) to 0.01 centimeter (0.004 inches).

In one embodiment, the printheads 60, 62, 64, 66 may be operated at 100 to 150 volts at a frequency ranging from 2 to 160 kHz. A particularly suitable combination for operating at 366 MPM a web speed of 1200 FPM using these printheads would be 140 volts at 24 kHz. A particularly suitable combination for operating at a web speed of 100 FPM would be 140 volts at 2 kHz. The nominal drop mass of each droplet ejected by the printheads is measured to be about 80 ng (the standard drop mass specification for the printhead). In one aspect, the resolution of the printheads 60-66 is set at 100 dpi and the outer cover web 42 is run at a speed of from (100 to 2,000 feet per minute) 30.5 to 610 meters per minute. However, it is to be understood that other printheads at different operational settings may be used to obtain the image 11 of the present invention. The speed of the outer cover material web 42 can be even higher, for example, from about 610-1524 mpm (2,000 to 5,000 fpm). Application of ink by ink jet printheads to high speed substrates is also discussed in Sharma et al., U.S. patent application Ser. No. 10/330,515, entitled HIGH- SPEED INKJET PRINTING FOR VIBRANT AND CROCKFAST GRAPHICS ON WEB MATERIALS OR END-PRODUCTS, filed Dec. 27, 2002, the disclosure of which is incorporated herein by reference.

To produce the image 11 of the present invention, certain graphic design techniques can be employed. In one embodiment, certain design parameters are identified to operate in a CMYK color scheme at a relatively low resolution (measured in dpi) of the printheads 60, 62, 64, 66 to produce a sharp, commercially acceptable image. A first parameter is to eliminate black as used as shading within the image, and limit its use to separately outlining the central image. In other words, referring to FIG. 1, black would be used to outline the fishing dog and boat design element 11A and the sun design element 11B. The outline is indicated for several of the design elements 11A, 11B in the drawings (i.e., FIGS. 1 and 6A-6D) at 12. Although black is used in the illustrated embodiment to outline design elements 11A, 11B, other selected colors could be used for outlining. No black (or different color selected for outlining) is used for shading in the interior of the design element (11A or 11B) because black shading has been found to materially diminish the quality of the image, particularly at low printhead resolution. Moreover, an increased quantity of black is used for the outline. In the setup of the control software that will control the printheads 60-66, the threshold for black is set to maximum (as described more fully hereinafter). Maximizing the threshold for black has the practical effect of causing the maximum number of jets to fire in the black printhead 66 during printing. Because black is segregated into its own distinct region (i.e., surrounding a design element 11A, 11B), the high threshold of black enhances the black outline and sharpens the design element without degrading the quality of any other color in the design element. A second parameter is to set a minimum size of each separable design element (11A, 11B) to be no smaller than about 0.64 centimeter (0.25 inch). Moreover, the focal design element (in this case the fishing dog and boat 11A) should be at least about 3.81 centimeter (0.75 inch) tall. A focal design element is the design element that is perceived by the ordinary observer to be the central or most visually obtrusive design element of the image (in FIG. 1., the fishing dog in boat). Finally, original design work should be done in cyan, magenta, yellow and black (CMYK), the same four colors that are used for printing. By designing in CMYK, there is no degradation of the image that can otherwise be caused in the translation of images designed in red, blue and green into CMYK.

The following is an example of the techniques used for converting a computer designed image into a form that is used by Galaxy 256/80 MH printhead controller 48. The digital image 11 is opened in an image processing software such as Adobe Photoshop from Adobe Systems Incorporated having offices in San Jose, Calif. Other suitable software systems are well known in the art. If the image is to be printed at 100 dpi, no changes in the size of the image are necessary. However, if the image is to be printed at a higher resolution (e.g., 200 or 300 dpi), the image needs to be widened. It is noted that the image width (in the cross direction of the outer cover material) is limited to 256 dots or pixels (about 2.56 inches or 6.50 cm) because the image is printed in a single pass and this is the maximum dimension of the printhead. It will be understood that other, wider printheads having a different number of orifices and/or orifices with different spacings could be used without departing from the scope of the present invention. A wider printhead prints a wider (in the cross direction of the outer cover material) image. Moreover, printheads may be banked (placed side-by-side in the cross direction) to print a wider image. The image is split into each one of the four component process colors (cyan, magenta, yellow, black). The black color component of the image 11, the threshold is increased to its maximum value (255 in the Photoshop software). The black color image is then converted into a bit map with an output of 100 dpi using the diffusion dither mode of the program. The black color bit map is saved as a .tiff file with a name specifying that it is the black color component.

The other three colors are converted to bit maps with an output of 100 dpi using the halftone screen mode. The halftone screen mode should be set to have a frequency of 59 lines/centimeter (150 lines/inch), and employ the "ellipse" shape. The angles for the three color separations are cyan=75°, magenta=135° and yellow=0°. Each of these remaining three color component images is saved as its own .tiff file. The .tiff files can be merged into one printable image using a conversion program available from Spectra (T4tol program). Handling the conversion of the image in this way facilitates obtaining a sharp, commercially acceptable image at low resolutions. However, other settings could be used for converting the image without departing from the scope of the present invention.

The quality of the image printed must in the final analysis be acceptable to the consumer. It is possible to quantify certain aspects of the image that show that the image is of a good quality. This information includes the surface area of the substrate which is covered by the ink, the lightness of the color of the image and the color difference from the background on which it is printed.

Color is commonly measured by using spectrodensitometers, which measure reflected light and provide colorimetric data as will be described hereinafter. The light which is reflected in the visual range (i.e., having a wavelength of 400 nm to 700 nm) can be processed to give a numerical indication of the color. An example of such a device is the X-Rite 938 reflection spectrodensitometer available from X-Rite, Incorporated of Grandville, Mich. A suitable program for analyzing the data generated by this instrument is the X-Rite QA Master 2000 software available from X-Rite, Incorporated.

Color can be described generally in terms of three elements, hue, chroma (or saturation) and lightness (sometimes called value or brightness). Hue (h°) is the perceived attribute of a specific color that fixes the color's spectrum position and classifies it as blue, green, red or yellow. Chroma describes the vividness or dullness of a color. It is a measurement of how close the color is to either gray (a mixture of all colors) or to the pure hue. Chroma (C*) can be broken into two measurements: a* the measurement of the redness or greenness of the color; and b* the measurement of the yellowness or blueness of the color. The range for a* is from −60 to 60, with the range segment from 0 to 60 indicating increasing saturation of red as you approach 60, and the range segment 0 to −60 indicating increasing saturation of green as you approach −60. Chroma is defined as $C^* = (a^{*2} + b^{*2})^{1/2}$. Lightness is the luminous intensity of a color, or how close the color is to white or black and ranges in value from 0 (black) to 100 (white). All of these attributes can be determined using the aforementioned spectrodensitometer, and analyzed with the QA Master 2000 software. One way in which color data is commonly analyzed is to determine the difference of a measured color from a reference sample. This quantity is typically represented as "DE". Mathematically, DE is determined by the following equation:

$$DE = (\Delta L^2 + \Delta a^2 + \Delta b^2)^{1/2}$$

Figure 3:
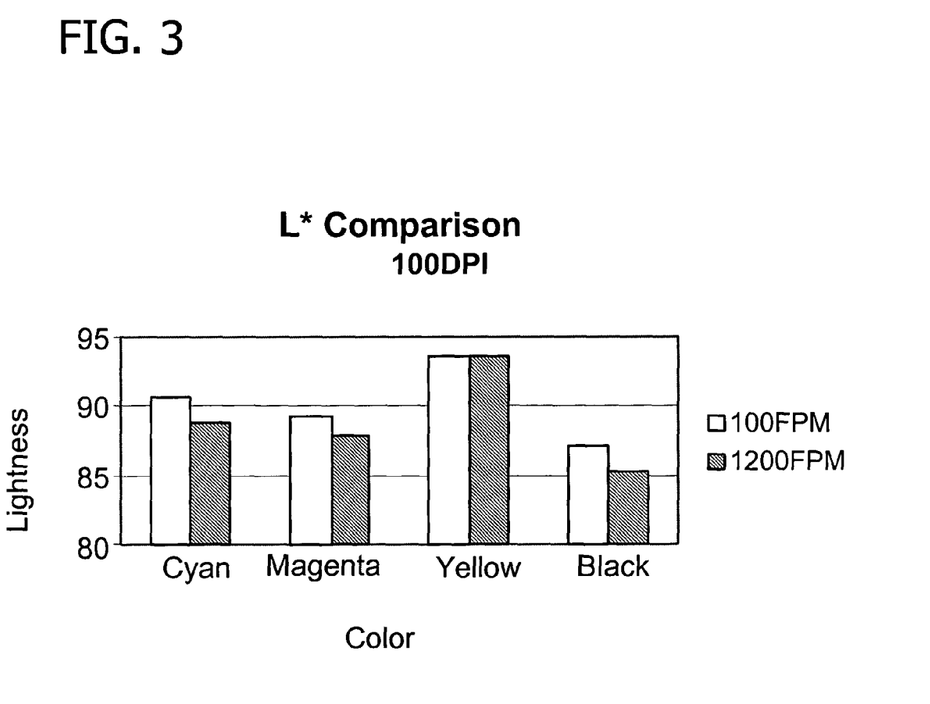
FIG. 3 is a bar graph comparing lightness of color blocks of the same color, each printed on a moving web of outer cover material for the diaper at a respective web speed.

Table 1 shows colorimetry data (specifically lightness L* and color difference DE) taken from blocks of each of the four colors (CMYK). These colors were separately applied to the exterior surface of outer cover material of the diaper 10 by the printheads operating at 140 volts and 2 kHz to 24 kHz, and at a resolution of 100 dpi. The threshold for each printhead was set to maximum. In other words, the printheads were controlled so that the maximum number of orifices available to fire and dispense ink at a given resolution (i.e., 100 dpi) would be fired. The data is given for web speeds of 30.5 mpm (100 fpm) and 366 mpm (1,200 fpm). The data for lightness (L*) is presented in the form of a graph in FIG. 3. Surprisingly, it may be seen that for each color (except yellow), the L* is a lower value at 366 MPM (1200 FPM) than at 30.5 MPM (100 FPM), which means that that color is darker or more vibrant at higher speeds, even though the printheads 60-66 are operating in the same manner with less output of ink. Due to the transparency and lightness of the yellow ink significant differences in the L* values are not measurable at these low resolutions. Other colorimetry data suggests that color differences are measurable and visually apparent in the samples printed with yellow.

Figure 4:
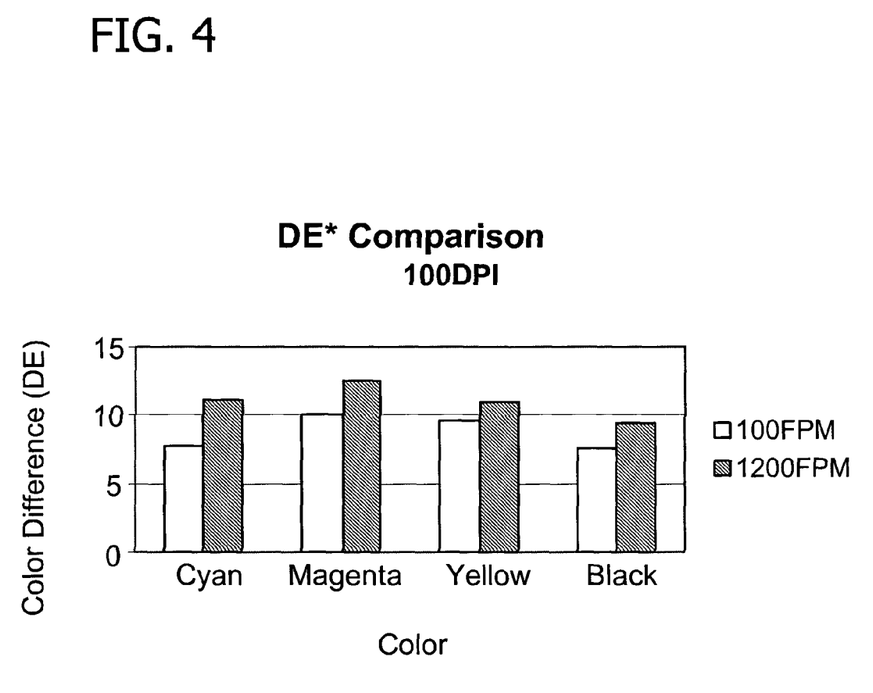
FIG. 4 is a bar graph comparing the color differences of the color blocks printed at the two different web speeds.

The color difference data (DE) is presented graphically in FIG. 4. Color difference is established by comparing the measured L*, a* and b* values of unprinted diaper outer cover material to L*, a* and b* values for the images printed on the same diaper outer cover material. In the illustrated embodiment, the outer cover material is white and has color values of a*=−0.54 and b*=0.97, and a lightness value of 94.17. It is also envisioned that white ink could be applied over a non-white outer cover material to achieve an image of the present invention. The difference for each value (L, a*, b*) from the baseline (the outer cover material) is used in the formula given above to determine DE. The graph in FIG. 4 shows that for all four process colors (CMYK), the difference from the outer cover material is surprisingly greater for the color blocks printed at 366 mpm (1,200 fpm) than for those blocks printed at 30.5 mpm (100 fpm). Thus, the image 11 of the present invention is more vibrant, brighter and stands out better visually even though it is formed at a higher web speed.

In one embodiment, criteria for the color difference to produce an acceptable image using cyan, magenta, yellow and black process colors at low resolution (100 dpi) applied to a substrate moving at high speed (366 mpm (1,200 fpm)) have been determined. The color difference (DE*) value for any cyan colored ink in the image as compared to a background color of the article on which the image is printed is at least about 6. The DE* value for any magenta colored ink in the image has a color difference (DE*) of at least about 9. The DE* value for any yellow colored ink in the image has a color difference (DE*) of at least about 8. The DE* value related to black colored ink or its equivalent in the image has a color difference (DE*) of at least about 6. Images made according to the principles of the present invention may have other DE* values without departing from the scope of the present invention.

TABLE 1

| Graphic | Speed | DPI | Voltage | L* | DE* |
| --- | --- | --- | --- | --- | --- |
| Outer Cover | NA | NA | NA | 94.17 | NA |
| Cyan | 100 | 100 | 140 | 90.72 | 7.72 |
| Magenta | 100 | 100 | 140 | 89.32 | 10.07 |
| Yellow | 100 | 100 | 140 | 93.58 | 9.59 |
| Black | 100 | 100 | 140 | 87.19 | 7.51 |
| Cyan | 1200 | 100 | 140 | 88.89 | 11.18 |
| Magenta | 1200 | 100 | 140 | 87.92 | 12.51 |
| Yellow | 1200 | 100 | 140 | 93.57 | 11.02 |
| Black | 1200 | 100 | 140 | 85.34 | 9.36 |

Figure 5:
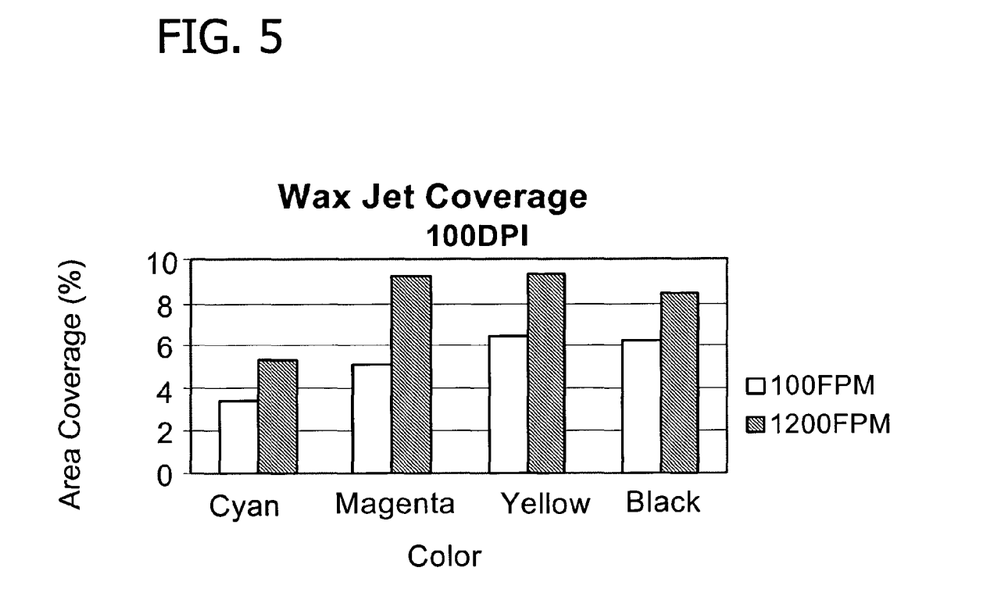
FIG. 5 is a bar graph comparing the coverage area ratio for ink applied to the substrate in the color blocks.

Without being held to any particular theory, it is believed that the image is darker, more vibrant and stands out more against the background of the outer cover 20 at higher feed rates under the conditions set forth above because there is a greater surface area of coverage of ink. Table 2 shows data taken from the cyan, magenta, yellow and black color blocks printed as described above. Data is shown for both blocks produced at 30.5 mpm (100 fpm) and 366 mpm (1,200 fpm). FIG. 5 presents this data graphically. As may be seen, a consistently greater cover area ratio is obtained at 366 mpm (1,200 fpm).

TABLE 2

COVERAGE RATIO

| Speed (FPM) | DPI | Color | Area | Standard Dev. |
| --- | --- | --- | --- | --- |
| 100 | 100 | C | 3.43 | 0.41 |
| 100 | 100 | M | 5.08 | 0.74 |
| 100 | 100 | Y | 6.43 | 0.51 |
| 100 | 100 | K | 6.19 | 0.63 |
| 1200 | 100 | C | 5.38 | 0.3 |
| 1200 | 100 | M | 9.21 | 0.95 |
| 1200 | 100 | Y | 9.35 | 0.42 |
| 1200 | 100 | K | 8.4 | 0.72 |

The data was acquired by taking images on a Zeiss KS400 Image Analysis system using a Zeiss Axioplan 2 Imaging microscope equipped with an Axiocam scientific charge-coupled device (CCD) camera (1300×1030 pixels, 8 bit RGB). These instruments are available from Carl Zeiss, Inc., having offices in Thornwood, N.Y. The field of view was 2.6 mm (0.1 in)×2 mm (0.08 in) (a 5× objective) in the transmission mode of the camera. The area coverage assessment was made from each 2.6 mm (0.1 in)×2 mm (0.08 in) field of view. At 100 dpi, each field would contain on the order of 80 droplets. To provide a baseline lighting level where the topology of the outer cover samples varies significantly, a maximum depth of field was obtained by closing down the condenser iris to its minimum setting. The auto-exposure function was set to 200 ms and the lighting level of an empty field of view (i.e., with no sample being supported on the instrument stage for viewing) including 0.32 centimeters (⅛ inch) cover glass was adjusted so that the image was balanced (being neither satureated or black). The sample was placed on the stage with the cover glass on top and the exposure was set to 700 ms providing good contrast and use of dynamic range.

Lighting conditions and microscopy mode (i.e., transmitted, reflected, etc.) may be varied, but should be such that the region between the top and bottom 1% of the image histogram occupies at least 25% of the camera range (64 levels in an 8 bit camera), but preferably 75% or higher. In the tests conducted herein, transmitted light was used. Approximately 20% of the surface area of the outer cover 20 was embossed, which resulted in large local changes in topology. Therefore, to achieve the best focus of the ink jet droplets and most accurate area estimation, images were acquired on the relatively flat regions between embossing patterns. Five or more regions were acquired for each of the color blocks (cyan, magenta, yellow and black).

The camera breaks down detected color (other than black) into red, blue and green channels, rather than cyan, magenta and yellow. Cyan reflects well in the green and blue channels but absorbs strongly in the red channel. Therefore, cyan is detected by subtracting the red channel from the combined green and blue channels according to the equation cyan=(B+G)/2−R. Magenta reflects well in red and blue, but absorbs strongly in green so it can be determined according to the equation magenta=(R+B)/2−G. Yellow reflects well in red and green, but absorbs strongly in blue so it can be determined according to the equation yellow=(R+G)/2−B. Other light/dark features, such as uncoated fibers are largely removed from the image. These images were subjected to a threshold for detecting only features brighter than 10 gray levels. The acquired black ink image differed in the detection of features by conversion to a gray scale image and subsequently thresholded for features under 50 gray levels (8 bit scale). Objects smaller than 50 pixels were discarded, and measurement of the field area coverage was performed on the remaining features.

Figure 7A:
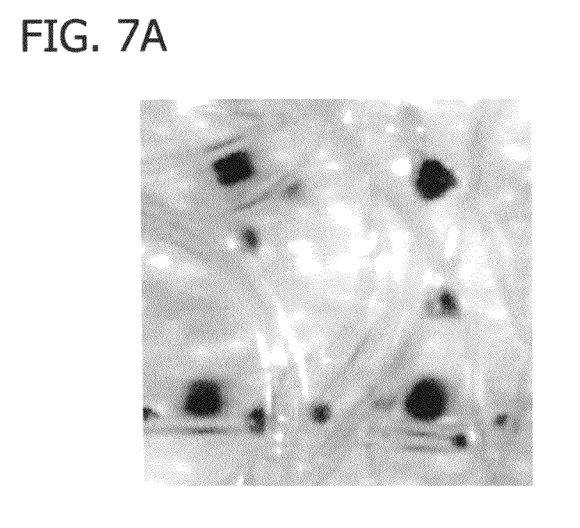
FIG. 7A is a photograph if a disbursement of ink on a substrate applied at 30.5 mpm (100 fpm) movement of the substrate.
Figure 7B:
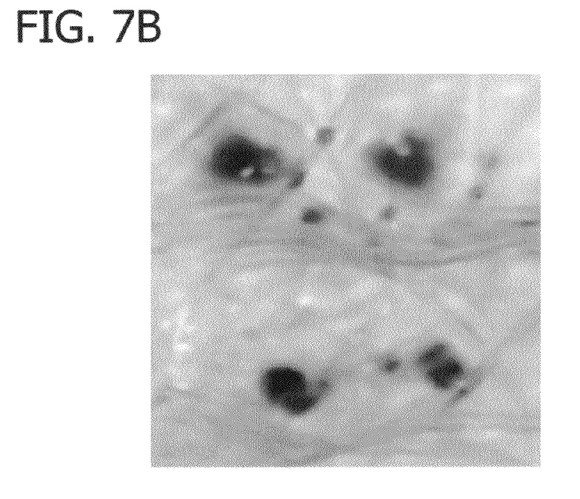
FIG. 7B is a photograph of a disbursement of ink on a substrate applied at 366 mpm (1,200 fpm) movement of the substrate.

Referring again to Table 2 and FIG. 5, it may be seen that the area of the outer cover material within the block covered by ink increased significantly at 366 mpm (1,200 fpm) over that obtained when running the outer cover material web at only 30.5 mpm (100 fpm). Microphotographs of the outer cover showing the disbursement of the ink drops confirm this finding. FIGS. 7A and 7B show the ink as applied to the outer cover material when applied at 30.5 mpm (100 fpm) and 366 mpm (1,200 fpm), respectively. The ink droplets on the outer cover material in FIG. 7B are seen to be more widely disbursed and hence to cover more area than FIG. 7A. The coverage area ratio increases although the outer cover material web is increased in speed from 30.5 mpm (100 fpm) to 366 mpm (1,200 fpm).

Some examples of acceptable coverage area ratios have been determined. In one instance, any area within an image having a cyan colored ink applied at maximum threshold thereto has a coverage area ratio of cyan colored ink of at least about 3%, any area having a magenta colored ink applied at maximum threshold thereto has a coverage area ratio of magenta colored ink of at least about 5%, any area having a yellow colored ink applied at maximum threshold thereto has a coverage area ratio of yellowed colored ink of at least about 6%, and any area having a black colored ink applied at maximum threshold thereto has a coverage area ratio of black colored ink of at least about 6%. In another example any area within an image having a cyan colored ink applied at maximum threshold thereto has a coverage area ratio of cyan colored ink of at least about 4%, any area having a magenta colored ink applied at maximum threshold thereto has a coverage area ratio of magenta colored ink of at least about 7%, any area having a yellow colored ink applied at maximum threshold thereto has a coverage area ratio of yellowed colored ink of at least about 9%, and any area having a black colored ink applied at maximum threshold thereto has a coverage area ratio of black colored ink of at least about 7%. In still a further example, any area within the image having cyan colored ink applied at maximum threshold thereto has a coverage area ratio of cyan colored ink of at least about 5%, any area having a magenta colored ink applied at maximum threshold thereto has a coverage area ratio of magenta colored ink of at least about 8%, and any area having a black colored ink applied at maximum threshold thereto has a coverage area ratio of black colored ink of at least about 8%.

When introducing elements of the present invention or the preferred embodiments() thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

The invention claimed is:

1. A mass produced absorbent article comprising an absorbent member adapted to retain liquid therein, at least one other component operatively connected to the absorbent member in a unit, and an image including at least one ink having the color of one of cyan, magenta, yellow and black, and at least one other ink having a different color of one of cyan, magenta, yellow and black, the image being printed in a non-contact manner on at least a portion of said at least one other component by ink jets at a resolution of about 100 dpi with said at least one other component moving under the ink jets at a speed of at least about 30.5 mpm (100 fpm), wherein any area in the image having a cyan colored ink applied at maximum threshold thereto has a coverage area ratio of cyan colored ink of at least about 3%, any area in the image having a magenta colored ink applied at maximum threshold thereto has a coverage area ratio of magenta colored ink of at least about 5%, any area in the image having a yellow colored ink applied at maximum threshold thereto has a coverage area ratio of yellowed colored ink of at least about 6%, and any area in the image having a black colored ink applied at maximum threshold thereto has a coverage area ratio of black colored ink of at least about 6%, and wherein each respective coverage area ratio is the percentage of any area in the image which is covered by the corresponding cyan, yellow, magenta or black colored ink applied thereto.

2. An absorbent article as set forth in claim 1 wherein any area in the image having a cyan colored ink applied at maximum threshold thereto has a coverage area ratio of cyan colored ink of at least about 4%, any area in the image having a magenta colored ink applied at maximum threshold thereto has a coverage area ratio of magenta colored ink of at least about 7%, any area in the image having a yellow colored ink applied at maximum threshold thereto has a coverage area ratio of yellowed colored ink of at least about 9%, and any area in the image having a black colored ink applied at maximum threshold thereto has a coverage area ratio of black colored ink of at least about 7%.

3. An absorbent article as set forth in claim 1 wherein any area in the image having cyan colored ink applied at maximum threshold thereto has a coverage area ratio of cyan colored ink of at least about 5%, any area in the image having a magenta colored ink applied at maximum threshold thereto has a coverage area ratio of magenta colored ink of at least about 8%, and any area in the image having a black colored ink applied at maximum threshold thereto has a coverage area ratio of black colored ink of at least about 8%.

4. An absorbent article as set forth in claim 1 further comprising a background on which the image is printed.

5. An absorbent article as set forth in claim 4 where in the background is white.

6. An absorbent article as set forth in claim 5 wherein said component comprises an outer cover, the background being defined by the color of the outer cover.

7. An absorbent article as set forth in claim 6 wherein the white background comprises a layer of white ink applied to at least a portion of the outer cover.

8. An absorbent article as set forth in claim 1 wherein the image includes at least one separable design element having a periphery and an interior, the interior being free of shading of black ink.

9. An absorbent article as set forth in claim 8 wherein said at least one design element is outlined in black ink.

10. An absorbent article as set forth in claim 9 wherein the black ink is applied at the highest threshold for a selected resolution.

11. An absorbent article as set forth in claim 8 wherein the image includes multiple separable design elements, none of the design elements being smaller than about 0.64 centimeters (0.25 inches) in height.

12. An absorbent article as set forth in claim 11 wherein one of the design elements constitutes a focal design element, the height of the focal design element being at least about 1.91 centimeters (0.75 inches).

13. An absorbent article as set forth in claim 1 wherein the inks are wax-based.

14. An absorbent article as set forth in claim 1 wherein the outer cover is made of an extensible material.

15. An absorbent article as set forth in claim 1 wherein the absorbent article is one of: a diaper, a training pant and an adult incontinence garment.

16. An absorbent article as set forth in claim 1 wherein a color difference (DE*) value for any cyan colored ink in the image as compared to a background color of said component on which the image is printed is at least about 6, the DE* value for any magenta colored ink in the image has a color difference (DE*) of at least about 9, the DE* value for any yellow colored ink in the image has a color difference (DE*) of at least about 8, and the DE* value of any black colored ink in the image has a color difference (DE*) of at least about 6.

17. An absorbent article as set forth in claim 1 further comprising an overlay covering the image.

18. An absorbent article as set forth in claim 17 wherein the overlay comprises a clear, non-pigmented ink applied over the top of the image.

19. A mass produced absorbent article comprising an absorbent member adapted to retain liquid therein, at least one other component operatively connected to the absorbent member in a unit, and an image including at least one ink having the color of one of cyan, magenta, yellow and black, and at least one other ink having a different color of one of cyan, magenta, yellow and black, the image being printed in a non-contact manner on at least a portion of said at least one other component by ink jets at a resolution of about 100 dpi with the outer cover moving under the ink jets at a speed of at least about 30.5 mpm (100 fpm), wherein a color difference (DE*) value for any cyan colored ink in the image as compared to a background color of said at least one other component on which the image is printed is at least about 6, the DE* value for any magenta colored ink in the image has a color difference (DE*) of at least about 9, the DE* value for any yellow colored ink in the image has a color difference (DE*) of at least about 8, and the DE* value for any black colored ink in the image has a color difference (DE*) of at least about 6, and wherein each respective color difference (DE*) is the difference for the corresponding cyan, yellow, magenta or black colored ink from a reference sample.

20. An absorbent article as set forth in claim 1 wherein the image contains ink applied to said at least one component by the ink jet with dots having a uniform volume of ink.

21. An absorbent article as set forth in claim 1 wherein the image comprises ink dots of generally uniform size.

22. An absorbent article as set forth in claim 1 wherein said at least one other component comprises a non-woven material, the image being disposed on the non-woven material.

* * * * *

UNITED STATES PATENT AND TRADEMARK OFFICE
CERTIFICATE OF CORRECTION

| | | |
|---|---|---|
| PATENT NO. | : 8,273,066 B2 | Page 1 of 1 |
| APPLICATION NO. | : 10/623030 | |
| DATED | : September 25, 2012 | |
| INVENTOR(S) | : Anderson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1497 days.

Signed and Sealed this
Fourteenth Day of October, 2014

Michelle K. Lee
*Deputy Director of the United States Patent and Trademark Office*